(12) United States Patent
Lu

(10) Patent No.: US 6,308,707 B1
(45) Date of Patent: Oct. 30, 2001

(54) VACUUM EQUIPMENT FOR MEDICAL TABLES

(76) Inventor: Li-Chow Lu, 18F-2, No. 2, Lane 175, Sec. 3, Shiou-Lang Rd., Chung-Ho City, Taipei Hsien (TW)

( * ) Notice: Subject to any disclaimer, the term of this patent is extended or adjusted under 35 U.S.C. 154(b) by 0 days.

(21) Appl. No.: 09/247,583

(22) Filed: Feb. 10, 1999

(51) Int. Cl.$^7$ .......................... A62B 19/00; A62B 23/02; A62B 7/10
(52) U.S. Cl. .................. 128/205.12; 128/205.19; 128/910; 128/205.27; 128/205.29
(58) Field of Search ................. 128/205.12, 205.19, 128/910, 205.27, 205.29, 204.12

(56) References Cited

U.S. PATENT DOCUMENTS

| | | | |
|---|---|---|---|
| 3,433,222 | * 3/1969 | Pinto | 128/202.13 |
| 3,721,067 | * 3/1973 | Agnew | 55/97 |
| 3,892,234 | * 7/1975 | Jones | 128/202.13 |
| 4,082,092 | * 4/1978 | Foster | 128/139 |
| 4,141,703 | * 2/1979 | Mulchi | 55/316 |
| 4,219,020 | * 8/1980 | Czajka | 128/207.13 |
| 4,446,861 | * 5/1984 | Tada | 128/205.19 |
| 4,699,046 | * 10/1987 | Bellieni | 98/115.4 |
| 4,787,298 | * 11/1988 | Hon | 98/115.4 |
| 4,895,172 | * 1/1990 | Lindkvist | 128/863 |
| 5,125,939 | * 6/1992 | Karlsson | 55/316 |
| 5,127,411 | * 7/1992 | Schoolman et al. | 128/863 |
| 5,226,412 | * 7/1993 | Winters | 128/206.12 |
| 5,253,641 | * 10/1993 | Choate | 128/200.14 |
| 5,510,871 | * 4/1996 | Biegler et al. | 354/300 |
| 5,513,632 | * 5/1996 | Nepon et al. | 128/205.19 |
| 5,553,606 | * 9/1996 | Chen | 128/202.13 |
| 5,636,627 | * 6/1997 | Rochester | 128/205.27 |
| 5,694,923 | * 12/1997 | Hete et al. | 128/204.18 |
| 5,701,883 | * 12/1997 | Hete et al. | 128/204.26 |
| 5,715,813 | * 2/1998 | Guevrekian | 128/205.12 |
| 5,738,148 | * 4/1998 | Coral et al. | 138/120 |
| 5,820,623 | * 10/1998 | Ng | 606/1 |
| 5,996,578 | * 12/1999 | MacGregor | 128/204.26 |

* cited by examiner

*Primary Examiner*—John G. Weiss
*Assistant Examiner*—Joseph F. Weiss, Jr.
(74) *Attorney, Agent, or Firm*—Dougherty & Troxell

(57) ABSTRACT

A vacuum system for medical tables, primarily comprises a universal arm, attached inhaler masks and a vacuum source. This equipment primarily places the inhaler masks at the sides of patient's mouth. Then, through the vacuum source, the mist surrounding the patient's mouth and the dirty air breathed out by the patient will be inhaled and clean air is released after filtering.

2 Claims, 7 Drawing Sheets

VACUUM EQUIPMENT FOR MEDICAL TABLES

BACKGROUND OF THE INVENTION (a) Field of the Invention

This invention, a vacuum equipment for medical tables, in particular, vacuum equipment used in medical tables' environmental hygiene so as to lessen the possibility of doctors and nursing staffs from contracting infectious diseases.

(b) Description of the Prior Art

Accordingly, when doctors are treating their patients, for health concern, the doctors generally will wear masks as protection from their patients; also, particularly in the process of dental treatment, grinding teeth is the commonest treatment for teeth, however, when the teeth of a patient were ground, the rotation of grinding machine will produce centrifugal force which then causes the saliva and blood to be spit out from the patient's mouth, the saliva and blood will mix with the air and form a mist that spreads all over in the air. Also, for ear, nose and throat treatment and out-patient service, endoscope and diagnosis of tubercular patients, if the patient is infected with high risk infectious diseases that can be contracted through saliva, the doctors cannot ascertain that they have actually blocked the infectious bacteria with only the masks. In addition, the doctors always find themselves being spitted all over by the patients after the treatment, it is absolutely not healthy and they will become one of the groups that are in the great risk of being infected.

Furthermore, the other patients and the nursing staff may not wear masks and hence the hospitals have become a good place to transfer infectious diseases.

SUMMARY OF THE INVENTION

In view of this, the inventor has devoted research effort and discovered that by placing vacuum equipment at the side of patients' beds, the dirty air breathed out from the patients' lungs and mist spit out from the mouths will be inhaled by the said vacuum equipment and clean air will be released from the equipment after filtering. Consequently, the possibility of contracting infectious diseases from hospitals will be lowered.

For these reasons, the main objective of this invention is to provide vacuum equipment for medical tables that primarily comprises a universal arm, inhaler masks that are attached separately to two sides of the tube and a vacuum cleaner. This equipment has primarily placed inhaler masks at the side of patient's mouth, then, through the vacuum cleaner, the mist that surrounds the patient's mouth will be inhaled and clean air is released after filtering, consequently, the possibility of contracting infectious diseases is lowered.

Another objective of this invention is to provide a vacuum equipment for medical tables which has attachable and disposable inhaler masks. The inhaler masks are disposable and will not infect other persons because of having contact with the patients.

The following detailed explanations will make the other objectives of this invention and the detailed structure become clearer, at the same time, with reference to the enclosed drawings, one will have more understanding on the technology and contents of this invention.

DETAILED DESCRIPTION OF THE PREFERRED EMBODIMENT

Figure 1:
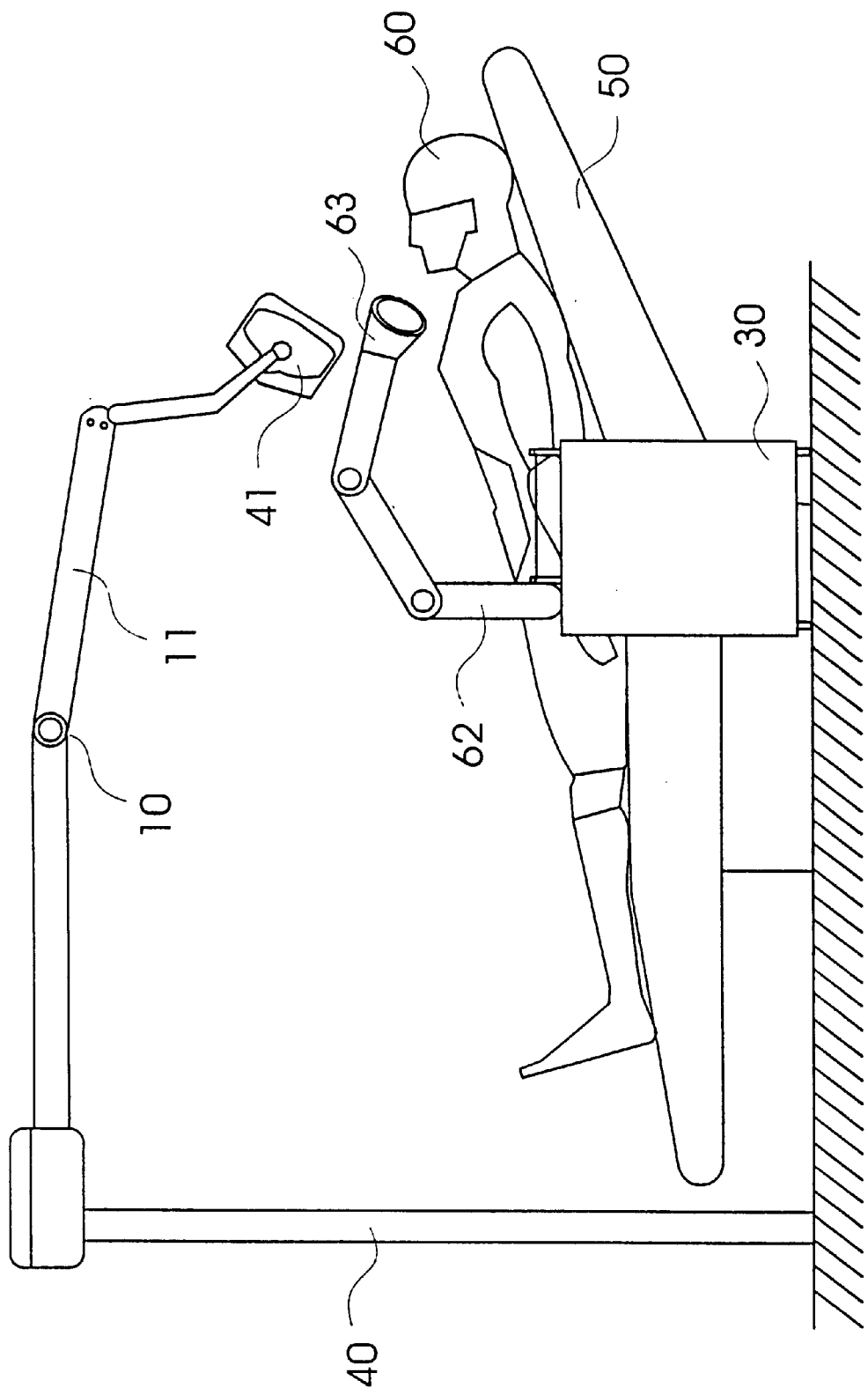
FIG. 1 is a drawing of this invention.

As illustrated in FIG. 1, this invention of vacuum equipment for medical tables mainly comprises a universal arm 10, a spotlight 41 secured to the end of universal arm 10, disposable masks 63 that are respectively attached to the end of tube 62 and vacuum device 30.

Figure 7:
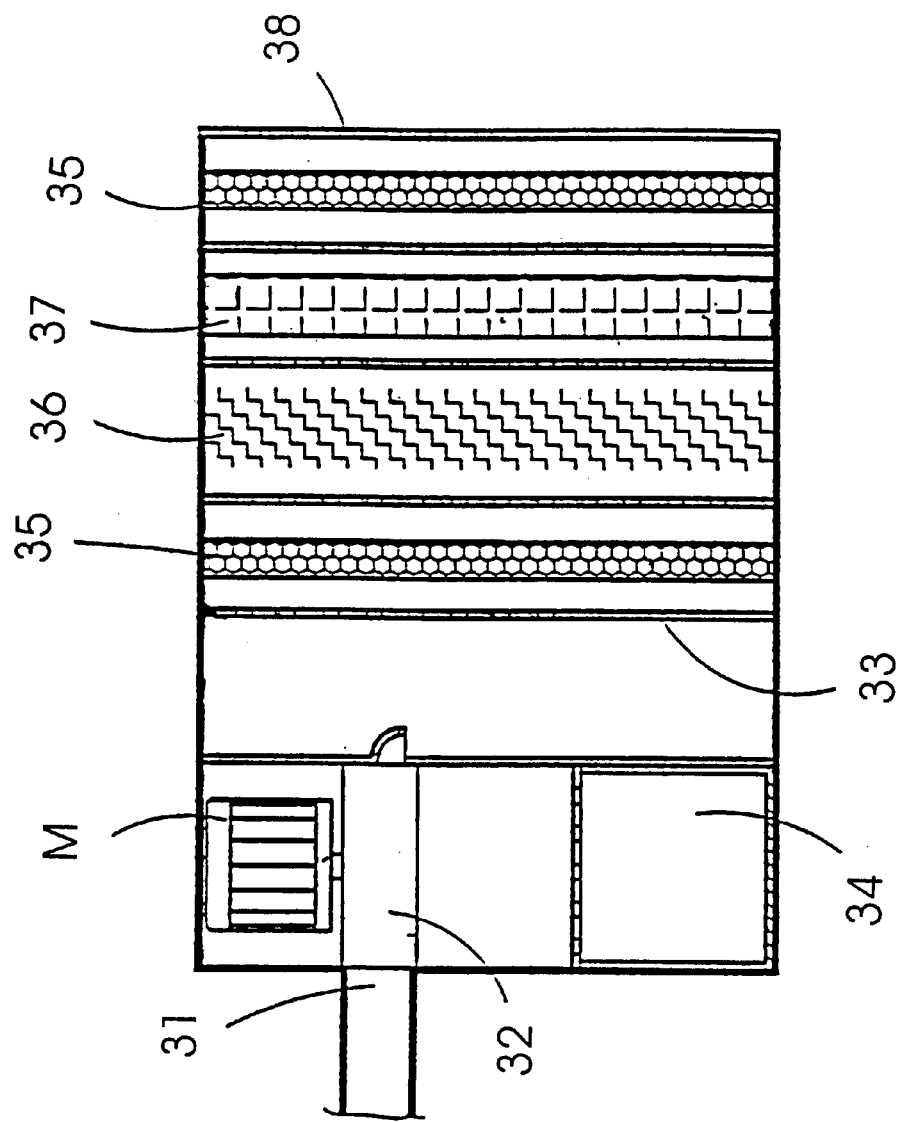
FIG. 7 is an illustration of various filters inside the vacuum cleaner for this invention.

The universal arm 10 is assembled by several hollow pipes 11. The joint between two pipes 11 can be bent to the appropriate angle so that the front end and the back end of the universal arm 10 can be adjusted to any coordinates that is within a suitable distance. The end of universal arm 10 is either attached to stand post 40 or installed at one side of table 50. Also, a pipe 11 is attached to the front end of universal arm 10 and connected to the spotlight 41. The disposable mask 63 can be adjusted to various angles through tube 62. The interior of tube 62 is smooth and glossy in order to maintain the tube clean and to avoid noise in the tube. The vacuum cleaner 30 has an air inlet 31 as shown in FIG. 7. A motor M is connected to the air inlet 31 and there is a fan 32 at the output of motor M. In addition, the partition nets 33 have divided the interior of vacuum cleaner 30 into several compartments. There are many holes on these partition nets which allows passage of air from one compartment to another. Beneath fan 32 is water and dirt reservoir compartment 34. After the above mentioned fan 32 is operated, the produced inhalant whirlwind will collect together impurities and dirt to the water and dirt reservoir compartment 34, the compartments beside the water and dirt reservoir compartment 34 are arranged in order as filter 35, ultraviolet rays 36, and active carbon 37. These compartments have filter materials that will filter impurities drawn in by the fan 32. The last section is an air outlet 38 that releases clean air.

This equipment is designed such that the important universal arm 10 is attached to stand post 40 so that the equipment can be integrated directly with the table 50 in production or installed to the side of table 50.

The other embodiment of this invention is shown in FIG. 2–FIG. 5, in order to satisfy various different needs, this invention also can integrate mask 20 and spotlight 42 on stand post 40 into one piece. The tubes that connect the part to vacuum source 30 are hidden inside the post. When the spotlight 42 approaches the patient 60, the integrated equipment and the non-integrated one will show similar effects.

Figure 2:
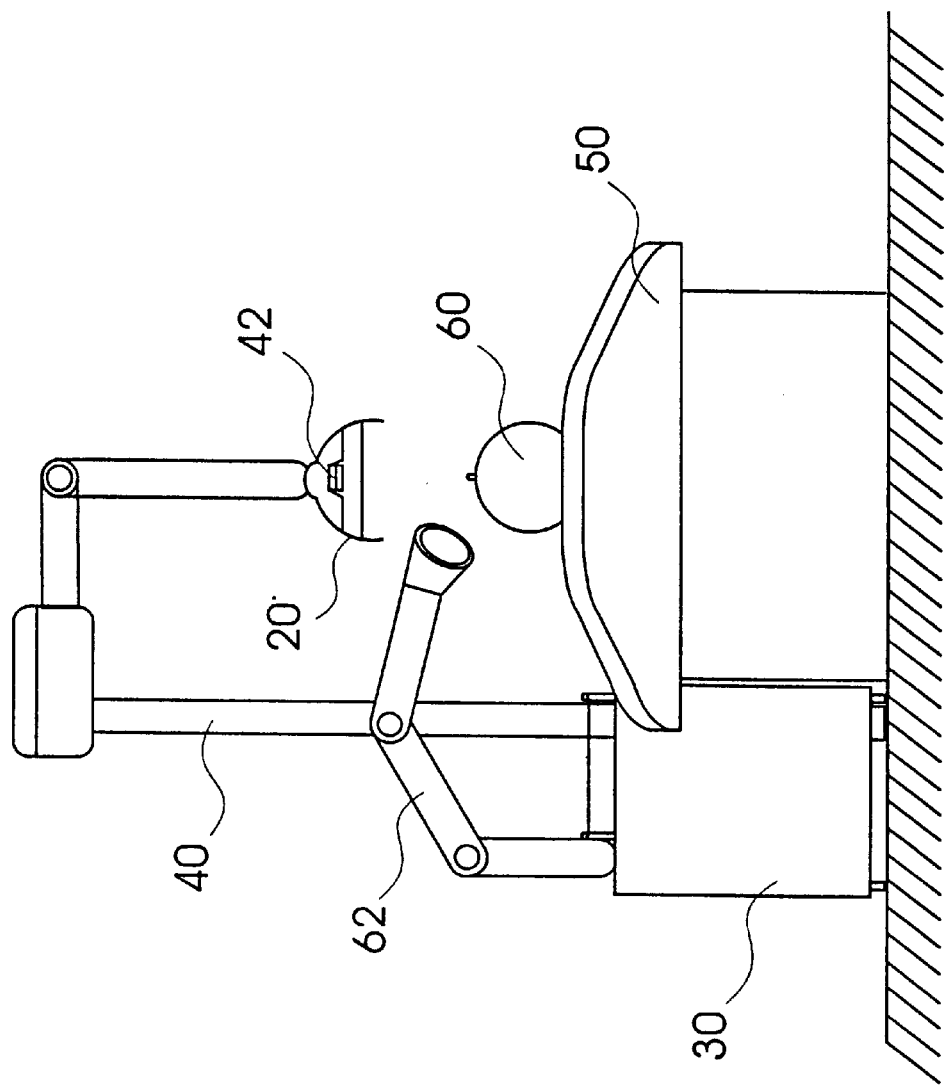
FIG. 2–FIG. 5 are operating drawings for this invention.
Figure 3:
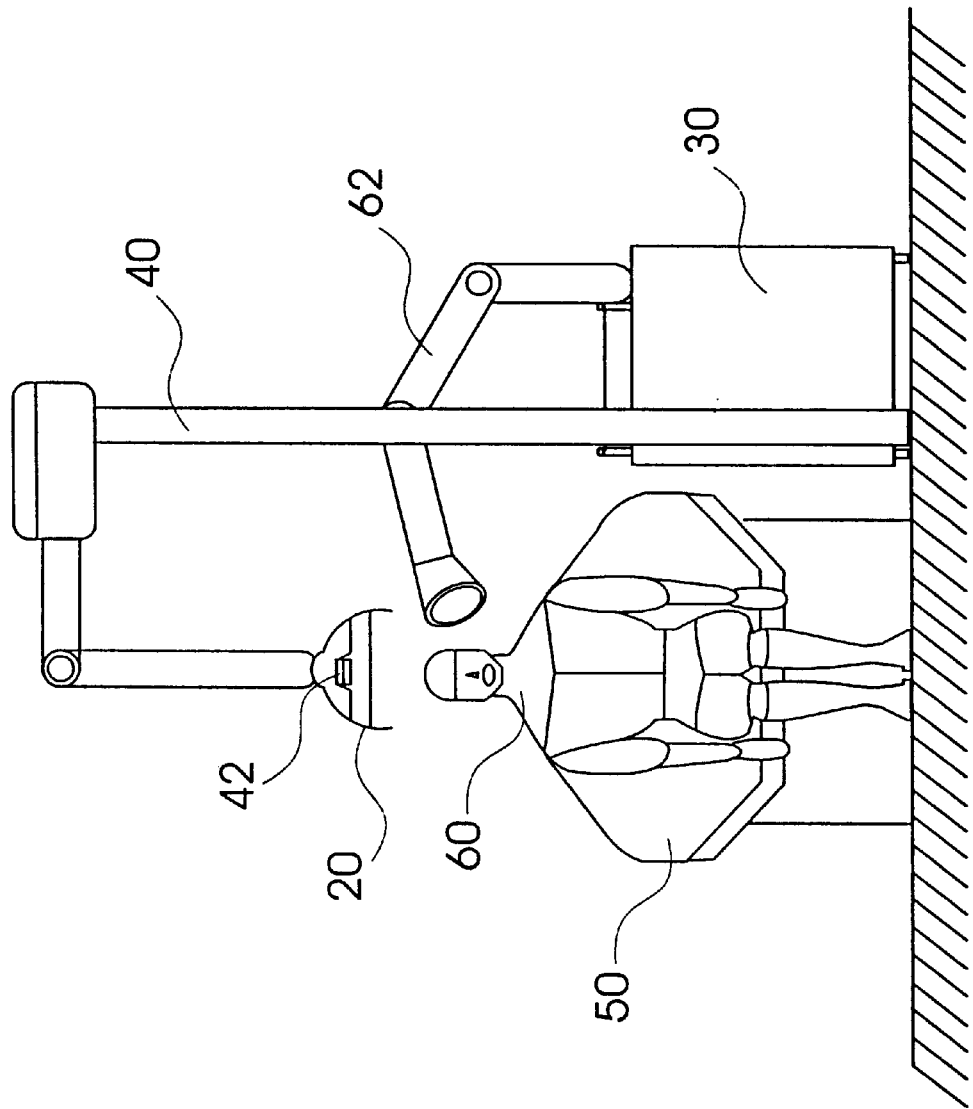
Figure 4:
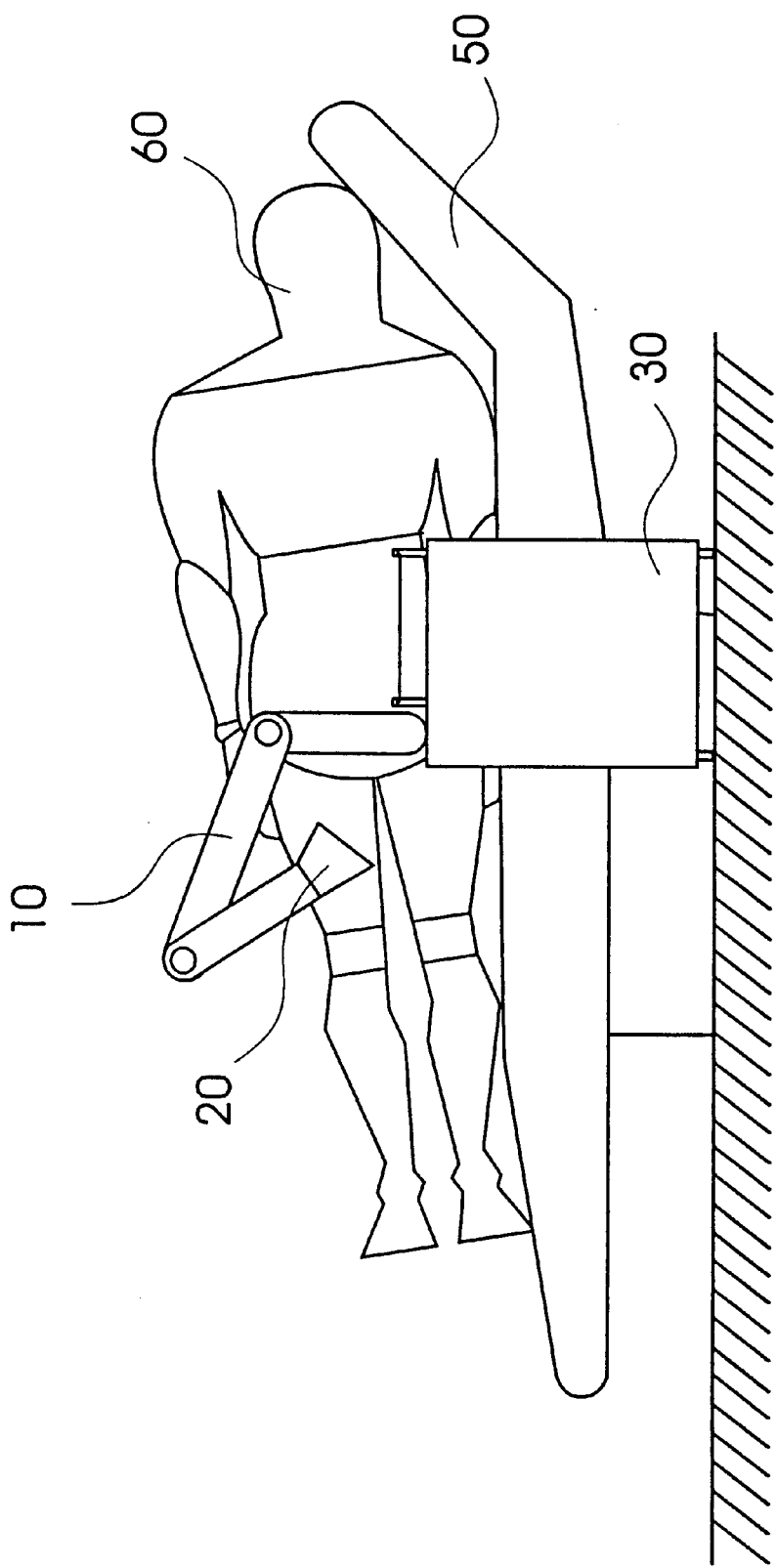
Figure 5:
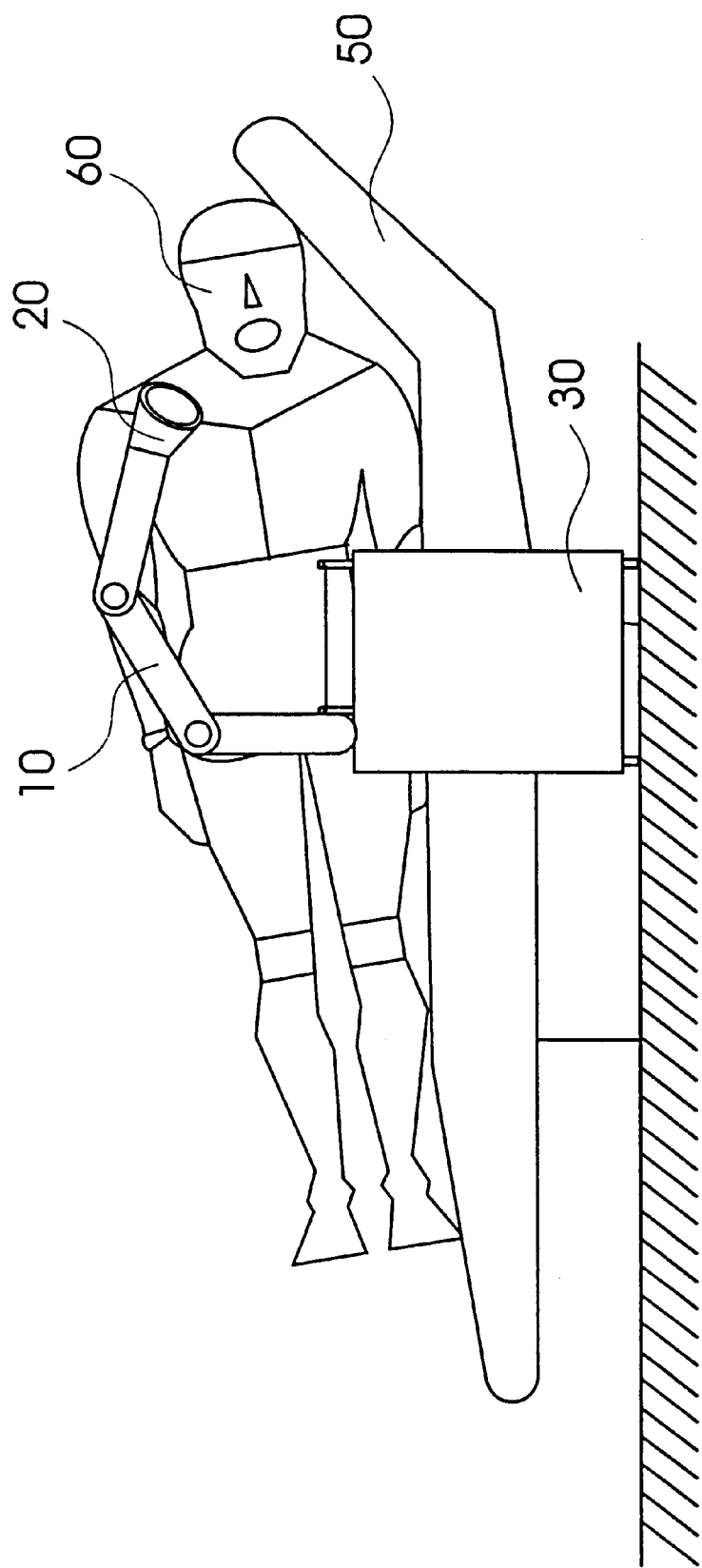
Figure 6:
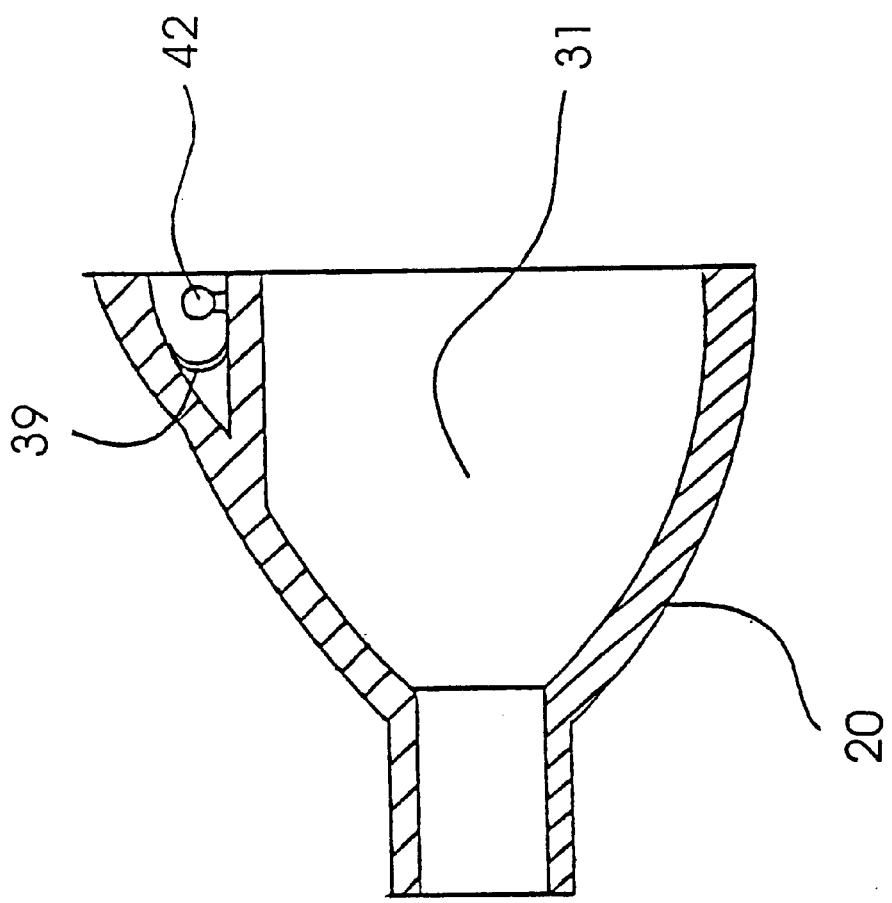
FIG. 6 is a drawing of an inhaler mask of this invention.

As shown in FIG. 2, when this invention is used in practice, the universal arm 10 will be twisted and the mask 20 is shifted right to the front of patient 60. When the dentists treat the teeth of patient 60 or the doctors diagnose their patients, the saliva and blood spit emanating from the patients' mouths will be sucked into the vacuum cleaner 30 by mask 20 (as shown in FIG. 7). As explained earlier, the operation of fan 32 will produce a whirlwind which then causes the blood and saliva to hang on the surface of walls and gather together at water and dirt reservoir 34. Thereafter, the remaining little impurities will be filtered, disinfected, and deodorized by passing through filter 35, ultraviolet rays 36, active carbon 37, and the clean air will be released finally. For illumination purposes, a spotlight comprising a bulb 42 and a reflector 39 are mounted on the mask 20. The mask may be one that is disposable.

From the above descriptions, it is understood that since this invention is designed for the use in various working environments, and hence, it may have a variety of designs. For example, the universal arm may be mounted to a stand post, or the universal arm may be installed at the side of the table. The mask and spotlight may be integrated together. These modifications are inventive and practical to satisfy the different environments.

From the above description, this invention is used to remove bacteria that is produced and spread over the air in the process of treating patients so that the hygiene safety for doctors and staffs as well as the hygiene inside hospitals can be improved. Consequently, the rate of infection will be reduced.

The above mentioned vacuum equipment of medical tables is a better example of implementing this invention. Nonetheless, it is not the only way to implement this invention, the actual variations, removal and amendment of this invention should not deviate from the following scope of the claims.

What is claimed is:

1. A recirculating vacuum system for increasing air hygiene in a medical examination room comprising:

a) a vacuum device located within the medical examination room, the vacuum device having: a motor driving a suction fan located adjacent to an air inlet such that the fan produces a suction whirlwind; a water and dirt reservoir compartment; a pair of spaced apart filters, an ultraviolet ray device and an active carbon layer located between the spaced apart filters; and an air outlet located within the medical examination room;

b) a hollow, universal arm having a first end communicating with the air inlet and having a second end;

c) a mask mounted on the second end of the hollow universal arm, the mask having an opening communicating with the hollow, universal arm, whereby the suction whirlwind draws mist from a patient in the examination room into the vacuum device through the mask and the hollow universal arm, the whirlwind separating water and dirt from the mist, the mist then passing through the filters, the ultraviolet ray device and the active carbon layer before returning to the examination room through the air outlet; and d) a spotlight mounted within the mask.

2. The recirculating vacuum system of claim 1 further comprising a stand post mounted on the vacuum device wherein the hollow, universal arm is mounted on the stand post.

* * * * *